US010976225B2

(12) United States Patent
Rackus et al.

(10) Patent No.: US 10,976,225 B2
(45) Date of Patent: Apr. 13, 2021

(54) DMF METHOD AND SYSTEM FOR CONCENTRATING ANALYTE FROM LARGE VOLUMES INTO SMALLER VOLUMES USING MAGNETIC MICROPARTICLES

(71) Applicant: THE GOVERNING COUNCIL OF THE UNIVERSITY OF TORONTO, Toronto (CA)

(72) Inventors: Darius George Rackus, Basel (CH); Aaron Ray Wheeler, Toronto (CA)

(73) Assignee: THE GOVERNING COUNCIL OF THE UNIVERSITY OF TORONTO, Toronto (CA)

(*) Notice: Subject to any disclaimer, the term of this patent is extended or adjusted under 35 U.S.C. 154(b) by 232 days.

(21) Appl. No.: 16/089,825

(22) PCT Filed: Mar. 31, 2017

(86) PCT No.: PCT/CA2017/050399
§ 371 (c)(1),
(2) Date: Sep. 28, 2018

(87) PCT Pub. No.: WO2017/219122
PCT Pub. Date: Dec. 28, 2017

(65) Prior Publication Data
US 2019/0376881 A1  Dec. 12, 2019

Related U.S. Application Data

(60) Provisional application No. 62/317,042, filed on Apr. 1, 2016.

(51) Int. Cl.
*G01N 1/40* (2006.01)
*G01N 33/543* (2006.01)
(Continued)

(52) U.S. Cl.
CPC .......... *G01N 1/40* (2013.01); *B01L 3/502761* (2013.01); *B01L 3/502792* (2013.01);
(Continued)

(58) Field of Classification Search
CPC ..... B01L 2200/0668; B01L 2300/0645; B01L 2300/0816; B01L 2300/089;
(Continued)

(56) References Cited

U.S. PATENT DOCUMENTS 8,927,296 B2    1/2015 Sista et al.
2003/0205632 A1  11/2003 Kim et al.
(Continued)

FOREIGN PATENT DOCUMENTS

CN    101351270      10/2005
CN    204017444 U    12/2014
(Continued)

OTHER PUBLICATIONS

Rackus et al. Lab on a Chip, vol. 17, Jun. 12, 2017, pp. 2272-2280.*
(Continued)

*Primary Examiner* — Maureen Wallenhorst
(74) *Attorney, Agent, or Firm* — Hill & Schumacher

(57) ABSTRACT

Disclosed herein is a method and system for concentrating analyte from large sample solutions using a combination of magnetic microparticles on a digital microfluidic device using virtual channels. Virtual channels are produced by applying voltages to a series of driving electrodes of the DMF that connect a reservoir of solution situated just outside of the DMF device to a fluid exit location. The magnetic microparticles are first exposed to a liquid sample containing the analyte whereupon analytes are bound by analyte specific receptors on the microparticles. By flowing these solutions of magnetic particles through virtual channels in DMF device, large volumes can be processed,
(Continued)

regardless of the total capacity of the DMF. Engaging a magnet underneath the DMF device while a suspension of magnetic microparticles is flowed through the virtual channel causes the microparticles to become immobilized and the supernatant solution is removed. The isolated magnetic microparticles can then be resuspended in a much smaller volume and further processed on the DMF device for whatever application, thereby significantly increasing the concentration of the analytes in the small droplets compared to the original liquid solution.

23 Claims, 6 Drawing Sheets

(51) Int. Cl.
 *B01L 3/00* (2006.01)
 *B82Y 25/00* (2011.01)
(52) U.S. Cl.
 CPC ..... *G01N 1/4077* (2013.01); *G01N 33/54326* (2013.01); *G01N 33/54333* (2013.01); *B82Y 25/00* (2013.01); *G01N 2001/4038* (2013.01); *Y10T 436/2575* (2015.01)
(58) Field of Classification Search
 CPC ......... B01L 2300/126; B01L 2300/165; B01L 2400/0406; B01L 2400/0427; B01L 2400/043; B01L 2400/0487; B01L 3/502761; B01L 3/502792; B82Y 25/00; B82Y 30/00; G01N 1/40; G01N 1/4077; G01N 2001/4038; G01N 33/543; G01N 33/54326; G01N 33/54333; Y10T 436/25; Y10T 436/25375; Y10T 436/255; Y10T 436/2575
 USPC ......... 436/518, 526, 63, 149, 150, 174, 177, 436/178, 180; 422/98, 502, 503, 504, 422/505, 527; 435/7.1, 287.1, 287.2, 435/287.3
 See application file for complete search history.

(56) References Cited

U.S. PATENT DOCUMENTS

| 2009/0283407 | A1  | 11/2009 | Shah et al. |
| 2010/0123457 | A1  | 5/2010  | Shinoda |
| 2011/0091989 | A1* | 4/2011  | Sista ............... G01N 35/0098 436/174 |
| 2012/0154886 | A1  | 6/2012  | Heikenfeld et al. |
| 2012/0168309 | A1  | 7/2012  | Heikenfeld et al. |
| 2013/0288254 | A1  | 10/2013 | Pollack et al. |
| 2015/0119285 | A1  | 4/2015  | Hong et al. |
| 2015/0377831 | A1  | 12/2015 | Wheeler et al. |
| 2018/0243743 | A1* | 8/2018  | Perroud ............ B01L 3/502715 |
| 2019/0168223 | A1* | 6/2019  | Soto-Moreno ........ H01L 21/768 |
| 2020/0108395 | A1* | 4/2020  | Dixon ..................... G01N 1/34 |

FOREIGN PATENT DOCUMENTS

| CN | 104561260 A   | 4/2015 |
| WO | 2007041692    | 4/2007 |
| WO | 2011059512 A1 | 5/2011 |
| WO | 2014113598    | 7/2014 |

OTHER PUBLICATIONS

K. Aguilar-Arteaga, J. A. Rodriguez and E. Barrado, Analytica Chimica Acta, 2010, 674, 157-165.
K. Choi, A. H. C. Ng, R. Fobel and A. R. Wheeler, in Annual Review of Analytical Chemistry, vol. 5, eds. R. G. Cooks and E. S. Yeung, Annual Reviews, Palo Alto, 2012, vol. 5, pp. 413-440.
K. Choi, A. H. C. Ng, R. Fobel, D. A. Chang-Yen, L. E. Yarnell, E. L. Pearson, C. M. Oleksak, A. T. Fischer, R. P. Luoma, J. M. Robinson, J. Audet and A. R. Wheeler, Analytical Chemistry, 2013, 85, 9638-9646.
N. M. Lafreniere, J. M. Mudrik, A. H. C. Ng, B. Seale, N. Spooner and A. R. Wheeler, Analytical Chemistry, 2015, 87, 3902-3910.
N. S. Mei, B. Seale, A. H. C. Ng, A. R. Wheeler and R. Oleschuk, Analytical Chemistry, 2014, 86, 8466-8472.
A. H. C. Ng, K. Choi, R. P. Luoma, J. M. Robinson and A. R. Wheeler, Analytical Chemistry, 2012, 84, 8805-8812.
A. H. C. Ng, M. Lee, K. Choi, A. T. Fischer, J. M. Robinson and A. R. Wheeler, Clinical Chemistry, 2015, 61, 420-429.
M. H. Shamsi, K. Choi, A. H. C. Ng and A. R. Wheeler, Lab on a Chip, 2014, 14, 547-554.
Banerjee, A. et al., Microfluidics, BioMEMS, and Medical Microsystems IX, edited by Holger Becker, Bonnie L. Gray, Proc. of SPIE, vol. 7929, 2011.
Banerjee, A. et al., 15th International Conference on Miniaturized Systems for Chemistry and Life Sciences Oct. 2-6, 2011, Seattle, Washington, USA.
Banerjee, A. et al., Lab Chip, 2012, 12, 758.
Banerjee, A. et al., Encyclopedia of Microfluidics and Nanofluidics, DOI 10.1007/978-3-642-27758-0_1753-1, 2014.
Banerjee, A. et al., Micromachines 2015, 6, 172-185; doi:10.3390/mi6020172.
He, J. et al., Micromachines 2016, 7, 29; doi:10.3390/mi7020029.
He, J. et al., Analyst, 2014, 139, 3002-3008.
Shah, G. et al., Journal of Microelectromechanical Systems, vol. 18, No. 2, Apr. 2009.
Banerjee, A. et al., Thesis, University of Cincinnati, 2013.
Vestad, T. et al., J. Micromech. Microeng. 14 (2004) 1503-1506.
Wang, X. et al., Biomicrofluidics 7, 014107 (2013).
Wang, Y. et al., Transducers 2007—2007 International Solid-State Sensors, Actuators and Microsystems Conference.
International Search Report PCT/CA2017/050399 dated Aug. 3, 2017.
Brendon Seale et al: "Digital Microfluidics for Immunoprecipitation", Analytical Chemistry, vol. 88, No. 20, Oct. 4, 2016, pp. 10223-10230.
Darius G. Rackus et al: "A digital microfluidic device with integrated nanostructured microelectrodes for electrochemical immunoassays", Lab on a Chip, vol. 15, No. 18, Jan. 1, 2015, pp. 3776-3784.
Darius G. Rackus et al: "Electrochemistry, biosensors and microfluidics: a convergence of fields", Chemical Society Reviews, vol. 44, No. 15, Jan. 1, 2015, pp. 5320-5340.

* cited by examiner

DMF METHOD AND SYSTEM FOR CONCENTRATING ANALYTE FROM LARGE VOLUMES INTO SMALLER VOLUMES USING MAGNETIC MICROPARTICLES

FIELD

The present disclosure relates to a digital microfluidics (DMF) based method and system for concentrating analyte from large volumes into smaller volumes using magnetic-micro and nanoparticles having analyte specific receptors bound thereto.

BACKGROUND

Magnetic micro- and nanoparticles are particles with diameters on the micro- or nanometer length-scale (hereafter "microparticles") that have magnetic or paramagnetic cores making them susceptible to manipulation by magnetic fields. The surfaces of these particles can be functionalized with specific binding elements (e.g. nucleic acids, antigens, antibodies), also referred to as analyte specific receptors. Functionalized microparticles are used in a variety of applications including immunoassays, sample cleanup, and nucleic acid assays. Temporarily immobilizing magnetic particles in a magnetic field enables a user to change the solution the particles are suspended in as well as the volume in which the particles are suspended. Concentration of magnetic microparticles is particularly useful in contexts in which (a) the target analyte to be captured on the microparticles is a solute present at low concentration or a suspended particle present at low density (e.g., circulating tumour cells), and/or (b) the method of detection does not have sufficient sensitivity to detect the captured target.[1]

DMF is an emerging technology in which discrete liquid droplets are manipulated on the surface of an array of electrodes. DMF has numerous complementary differences relative to conventional enclosed-microchannel-based fluidics, including reconfigurability (a generic device format can be used for any application) and absolute control over all reagents. DMF is typically implemented in a "two-plate" format, in which droplets are sandwiched between a bottom plate (bearing an array of electrodes coated with an insulator), and a top plate (bearing a ground electrode not coated with an insulator).[2]

Recently, DMF has proven to be a useful tool for handling small volumes of magnetic microparticles.[3-8] Its open platform eliminates the potential for particles to clog the device (unlike in microchannels) and its reconfigurability means that a single chip can be used for a variety of applications in combination with appropriately functionalized particles.

To date, one limitation of DMF chips is the inability to work with large volumes, which limits the capacity to concentrate dilute solutes or suspended particles. The area of the underlying electrodes determines fluid volume on DMF chips and the total volume capacity of the chip is the sum of the area of all the electrodes multiplied by the gap distance between the bottom and top plates. As a result, the theoretical concentration factor possible on any chip is limited both by the total area of the DMF device and the area of the smallest electrode.

In practice, the concentration factor will be smaller than this theoretical factor because of limitations around the geometry of the device and the positioning of the magnet. To effectively concentrate magnetic microparticles on a DMF device by a factor of several orders of magnitude, the device must be able to process volumes far greater than the capacity of the device.

SUMMARY

Disclosed herein is a method for sequestering and concentrating an analyte from a volume of liquid sample to a droplet of reagent with a smaller volume. The method includes exposing magnetic microparticles coated with analyte specific receptors to the volume of liquid sample (which may be arbitrarily large) containing the analytes and incubating such that analytes are bound to receptors on the particles. The volume of liquid containing the magnetic microparticles is placed on or adjacent to electrodes on a digital microfluidic device. A virtual fluid flow channels is produced across the digital microfluidic device by activing a preselected pattern of driving electrodes with a preselected pattern of voltages across the digital microfluidic device from the reservoir to an exit location from which liquid is to be removed. At the same time a magnetic field is applied at a preselected holding location along the virtual fluid flow channel so that upon activating the preselected pattern of driving electrodes, liquid from the volume of liquid in the reservoir is moved from the reservoir along the virtual flow path. The magnetic microparticles with the analyte bound to the analyte specific receptors moving with the liquid from the reservoir, upon reaching the holding location, are held at the holding location by the magnetic field, and the remaining liquid flows to the exit location by means of a pump mechanism.

Once the magnetic particles have been pinned or held at the holding location, a droplet of a selected reagent is dispensed over the over the magnetic microparticles held at the holding location. This droplet of reagent has a much smaller volume compared to the original volume of liquid from which the analytes were extracted. The magnetic field may be removed either before the reagent droplet is added, or during addition of the droplet, or after addition of the reagent droplet. The droplet of reagent containing the magnetic microparticles is further processed by the DMF to ensure the magnetic particles are homogenously mixed with the droplet of reagent, for example by activating various driving electrodes to move the droplet around to induce mixing. The droplet of reagent containing the magnetic microparticles having the analytes bound thereto contains a higher concentration of the analyte as compared to a concentration of the analyte in the volume of liquid.

In an embodiment, the pumping mechanism may be an absorbent wicking medium (such as a tissue or piece of filter paper) located at the exit location, and once the virtual channel(s) are created by applying voltages to a series of electrodes that connect the reservoir to the exit location, the absorbent wicking medium then acts as a pump by wicking fluid through capillary forces.

A further understanding of the functional and advantageous aspects of the present disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
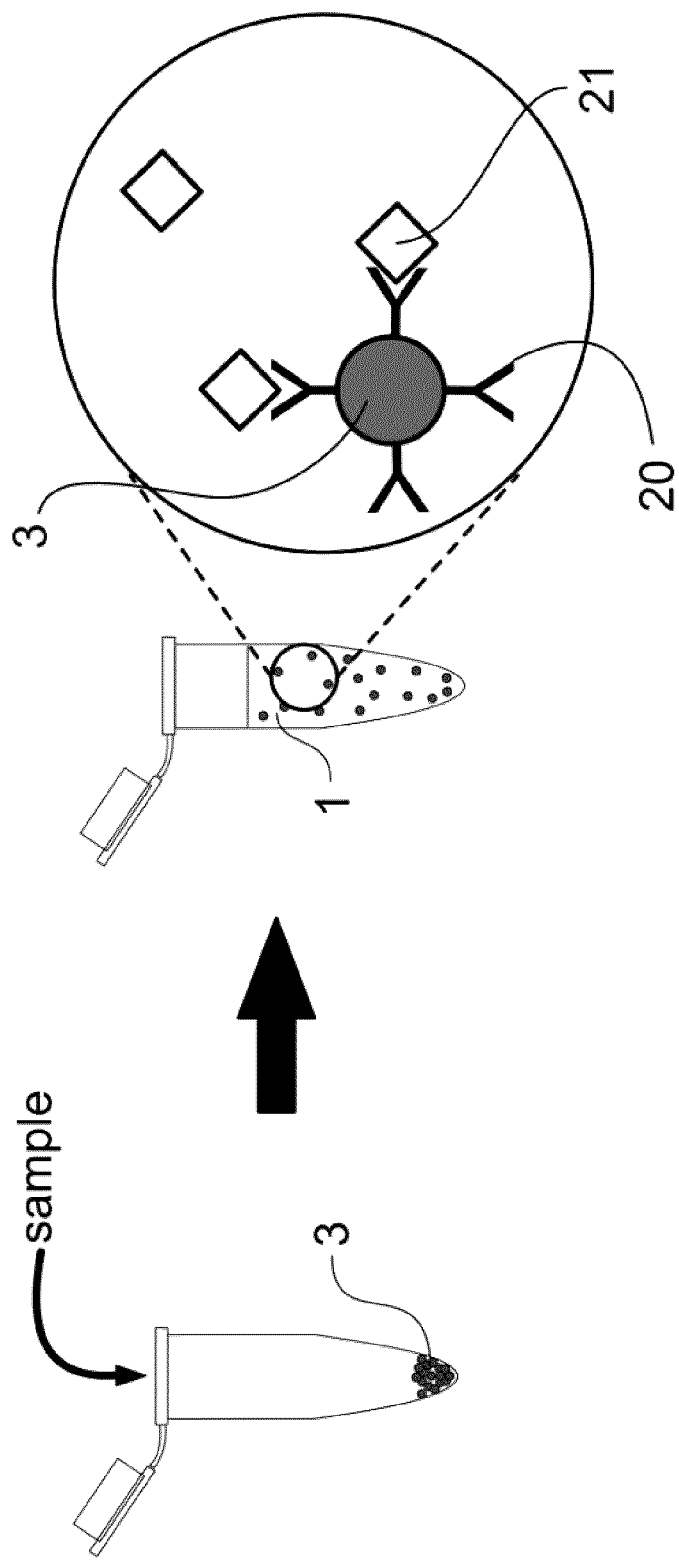
FIG. 1 Illustrates the capture of target analyte from a volume of liquid sample by magnetic microparticles coated with analyte specific receptors.

Various embodiments and aspects of the disclosure will be described with reference to details discussed below. The following description and drawings are illustrative of the disclosure and are not to be construed as limiting the disclosure. The Figures are not to scale. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood to one of ordinary skill in the art.

As used herein, the phrase "magnetic-micro and nanoparticles" refers to particles comprising paramagnetic iron oxide cores encapsulated with a polymer shell, such as polystyrene, ranging in diameter from 1 to 10 microns and functionalized with a capture moiety. This definition also describes magnetic nanoparticles with diameters on the order of 10-50 nanometers and are functionalized with a capture moiety.

Components of the method illustrated in are identified as follows:

CAPTIONS AND LABELS 1. volume of liquid sample (containing magnetic particles with bound analyte)
2. droplet of reagent of smaller volume
3. magnetic microparticles coated with analyte specific receptor (and bound analyte)
4. Digital Microfluidic Device
5. Virtual fluid flow channel
6. Driving electrodes
7. Exit location
8. Magnet/magnetic field
9. Holding location
10. Pump mechanism Pertaining to the DMF Device 11. top plate substrate (glass)
12. top plate electrode (indium tin oxide)
13. hydrophobic coating (Teflon, FluoroPel)
14. insulating dielectric (Parylene C)
15. reservoir (electrode)
16. bottom plate substrate (glass)

Miscellaneous 17. magnetic lens
18. "top plate"
19. volume of reagent
20. analyte specific receptor
21. analyte
22. hydrophilic stripe extending from the reservoir
23. hydrophilic stripe extending from the exit FIG. 1 Illustrates the capture of target analyte 21 from a volume of liquid sample 1 by magnetic microparticles 3 coated with analyte specific receptors 20. As can be seen, the method involves providing the magnetic microparticles 3 in a container and adding the large volume of liquid sample 1 into the container whereupon any analytes 21 present in the sample bind to their complimentary analyte specific receptor 20 bound to the magnetic particle.

Figures 2I, 2V:
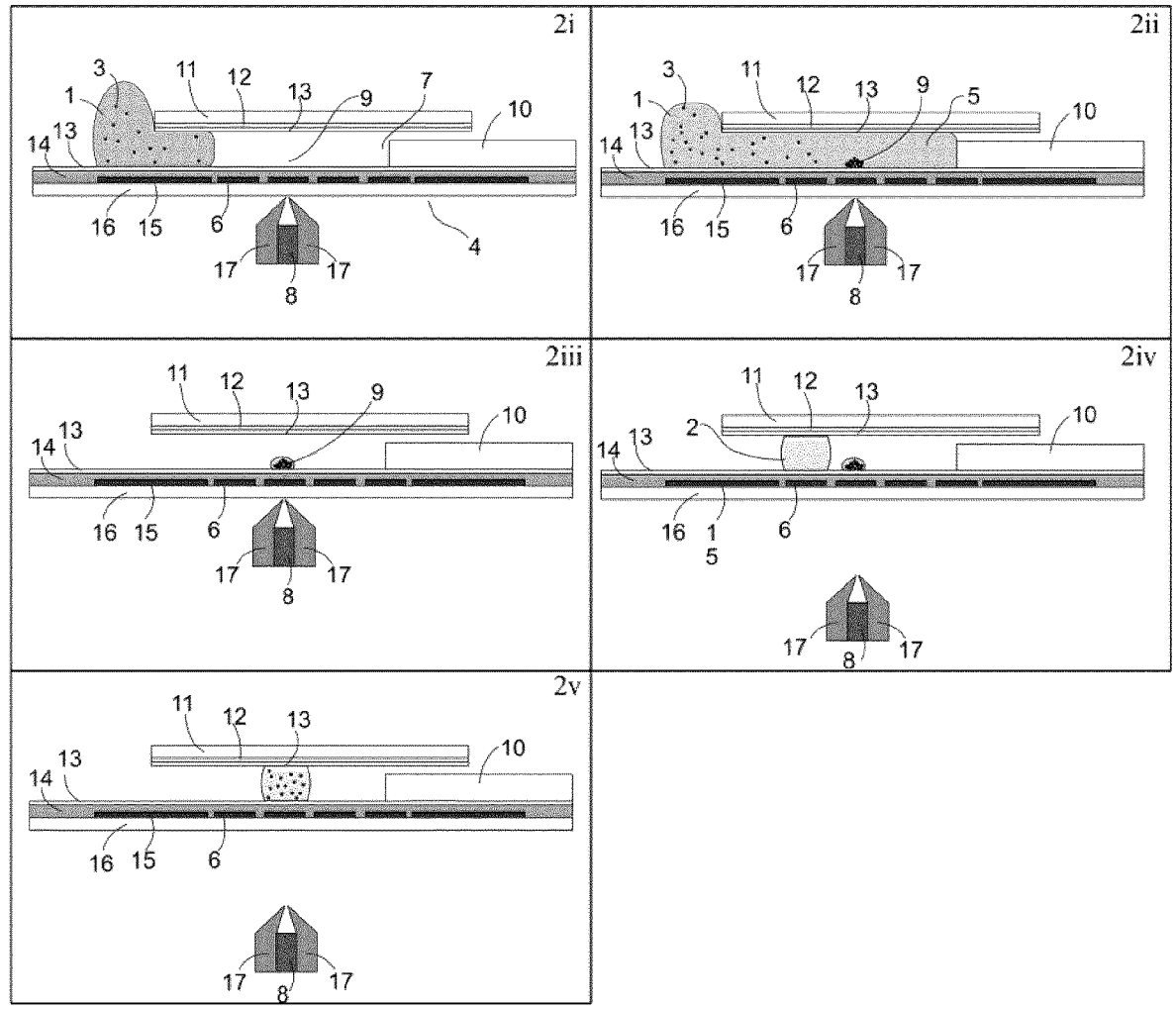
FIGS. 2*i*, 2*ii*, 2*iii*, 2*iv* and 2*v* show a cross sectional side view illustration (not to scale) of a DMF device demonstrating steps of the present method.

As can be seen from FIGS. 2*i* to 2*v* inclusive, DMF device 4 includes a pattern of driving electrodes 6, which when activated in a preselected pattern may be used to define a virtual fluid flow channel 5 (FIG. 3*ii*) across the DMF device 4 from reservoir 15 (which has its own set of electrodes) to an exit location 7. A magnet 8 with a lensing or field guiding structure 17 is located under preselected driving electrode(s) 6 to generate magnetic field above the preselected driving electrodes 6. The preselected location of the magnetic field defines a holding location 9 along the virtual fluid flow channel 5 above the preselected driving electrode(s) 6 such that upon engagement of the magnetic field any magnetic microparticles 3 passing along the flow channel 5 are immobilized by the magnetic field while the liquid of the sample continues to flow.

DMF device 4 includes a pump mechanism 10 located in one or more preselected position(s) 7 away from the electrodes 6 such that the liquid flowing along the virtual flow channel 5 is drawn off the DMF device 4 into a waste container. The pump mechanism 10 can be an active pump such as, but not limited to, a syringe, a peristaltic pump, or vacuum pump or a passive pump such as, but not limited to, an absorbent wicking material (filter paper or tissue paper, as two non-limiting examples).

The DMF device 4 comprises a bottom plate 16 and a top plate 18 where the bottom plate 16 contains a pattern of the driving electrodes 6 and the electrodes of reservoir 15 coated with an insulating dielectric layer 14 that is covered by a layer of hydrophobic material 13 and where the top plate 18 comprises a substrate 11 with a counter electrode 12 that is covered in a layer of hydrophobic material 13. Other potential embodiments (not shown) include reversing the orientation of plates (with "top" plate on bottom and vice versa), and/or with both plates covered with an insulating dielectric layer, and/or with multiple patterned driving and counter-electrodes on both plates, and/or in "single-plate" mode in which all driving and counter-electrodes are on a single bottom plate.

FIGS. 2i, 2ii, 2iii, 2iv and 2v show a cross sectional side view illustration (not to scale) of the DMF device 4 demonstrating the five steps of the method. In FIG. 2i the volume of liquid sample 1 containing the magnetic microparticles 3 which have analyte 21 (FIG. 1) bound thereto is placed on the DMF device 4 at a loading reservoir 15.

In FIG. 2ii a virtual fluid flow channel 5 is formed by actuating a sequence of driving electrodes 6 connecting the volume of liquid sample 1 with the pump mechanism 10 located at an exit location 7 to remove the liquid from the DMF device 4. Simultaneously the magnet 8 which has been prepositioned to apply a magnetic field to the holding location 9 under the preselected driving electrodes 6 and is engaged thereby immobilizing the magnetic particles 3 coated with analyte specific receptors 20 and bound analyte 21 in the holding location 9.

In FIG. 2iii the volume of liquid 1 has been removed by the pump mechanism 10 leaving behind the magnetic particles 3 coated with analyte specific receptors 20 and bound analyte 21 in the holding zone 9.

In FIG. 2iv the magnet 8 is moved away from the DMF device 4 thereby removing the magnetic field and a droplet of reagent 2 of smaller volume is dispensed onto the magnetic microparticles 3 in the holding location 9.

In FIG. 2v, the droplet of reagent 2 of smaller volume mixes with the magnetic microparticles 3 coated with analyte specific receptors 20 and bound analyte 21.

Figures 3I, 3V:
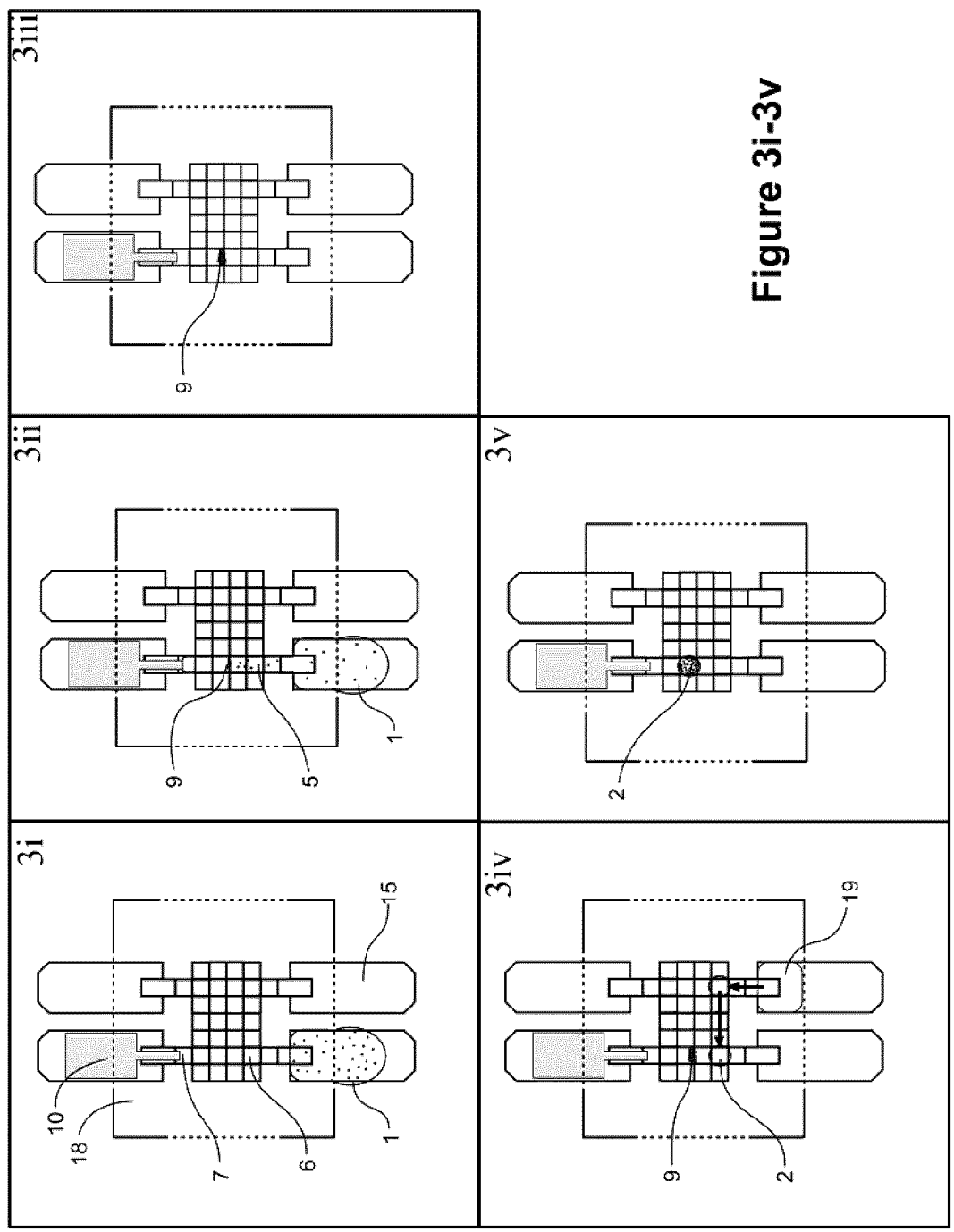
FIGS. 3*i*, 3*ii*, 3*iii*, 3*iv* and 3*v* show a top down view illustration of the DMF device demonstrating the five steps of the present method.

FIGS. 3i, 3ii, 3iii, 3iv and 3v show a top down view illustration of the DMF device 4 demonstrating the five steps of the method.

In FIG. 3i the volume of liquid sample 1 is placed on one or more of the reservoirs 15 outside of the top plate 18 and a portion of the volume of liquid sample 1 is drawn underneath the top plate 18. The pump mechanism 10 is situated underneath the top plate 18 and is adjacent to the exit location 7.

In FIG. 3ii the virtual fluid flow channel 5 is formed by activating the driving electrodes 6 connecting the volume of liquid sample 1 with the pump mechanism 10 located at an exit location 7 to remove the liquid from the DMF device 4. Simultaneously the magnet 8 which has been prepositioned to apply a magnetic field to the holding location 9 under the preselected driving electrodes 6 and is engaged thereby immobilizing the magnetic particles 3 coated with analyte specific receptors 20 and bound analyte 21 in the holding location 9.

In FIG. 3iii the pump mechanism 10 has removed the volume of liquid sample 1 leaving the magnetic microparticles 3 coated with analyte specific receptor 20 and bound analyte 21 in the holding location 9.

In FIG. 3iv reagent 19 (the same as reagent 2 but a larger volume in the reservoir 15) is loaded into one of the reservoirs 15 and a smaller droplet 2 of reagent is dispensed by actuating a series of preselected driving electrodes 6.

In FIG. 3v the smaller droplet 2 of reagent is mixed with the magnetic microparticles 3 coated with analyte specific receptors 20 and bound analyte 21 by actuating preselected driving electrodes 6 thereby causing mixing.

Results

In preliminary tests, 100 µL solutions containing magnetic microparticles at a density of $1.04 \times 10^7$ particles per mL were processed using the described method. The immobilized magnetic particles were resuspended in approximately 1.8 µL of buffer solution. The resulting density was measured to be $4.75 \pm 0.37 \times 10^8$ particles per mL, a concentration factor of approximately 45-fold. In theory, concentration factors of 100-fold and greater should be attainable by this described method, dependent only on the volume of liquid that can be added to the reservoir.

The absorbent wicking material can be chosen in order to control the flow rate of the virtual channel. Both the material and the geometry of the wick affect flow rates. In tests where 75 µL solutions were processed on a DMF device using a virtual channel and an absorbent wick, materials such as a double stack of 10 mm×10 mm Whatman No. 1 filter paper imbibed 75 µL in 60 seconds whereas a more absorbent material such as double stack of 10 mm×10 mm SureWick G028 glass fiber imbibes the same volume in 7 seconds.

In an alternative embodiment of the present method a one-plate DMF device where the driving electrodes and counter electrode are coplanar may be used. The one-plate device differs from the two-plate device in how the voltages are applied. Instead of applying the driving voltage to the bottom plate and the ground voltage to the top plate, the driving and ground voltages are both applied to adjacent electrodes on the bottom plate. In this embodiment the pre-concentration procedure remains the same as what was described above.

Figure 6:
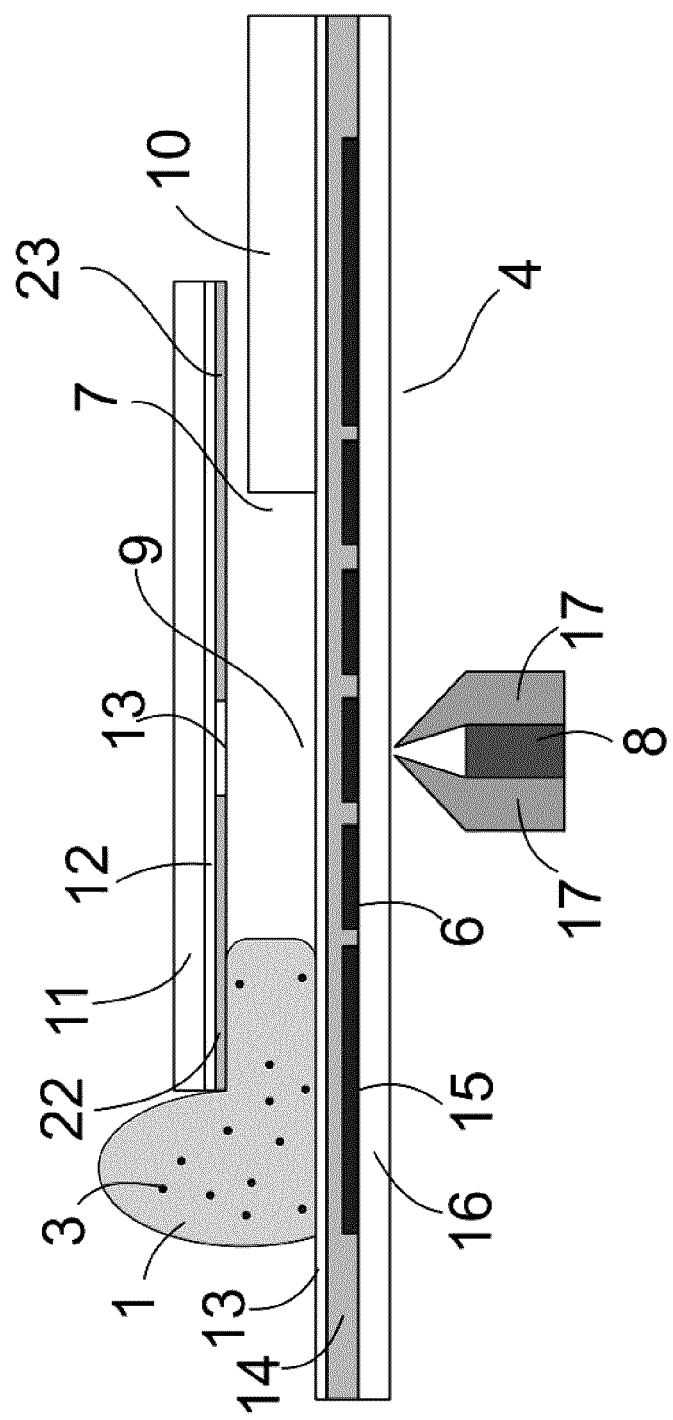
FIG. 6 shows a DMF device with hydrophilic stripes leading to and from the magnetic microparticle sequestering location.

Another embodiment of the present method relies on using a two plate DMF device with hydrophilic patterns on the top plate. This is illustrated in FIG. 6. In this embodiment one hydrophilic stripe 22 extends from the reservoir toward a pre-specified location where magnetic microparticles are to be sequestered on the DMF device. A second hydrophilic stripe 23 extends from the exit toward the same pre-specified location such that there is a gap between the two hydrophilic stripes which is less than the length of the underlying driving electrode on the bottom plate at the location where sequestering takes place. After loading the liquid volume sample, it is wicked along to the pre-specified location by the first hydrophilic stripe. By applying a voltage to the driving electrode at the pre-specified location, the liquid sample is bridged to the second hydrophilic stripe and imbibed by the passive pump.

Figure 4:
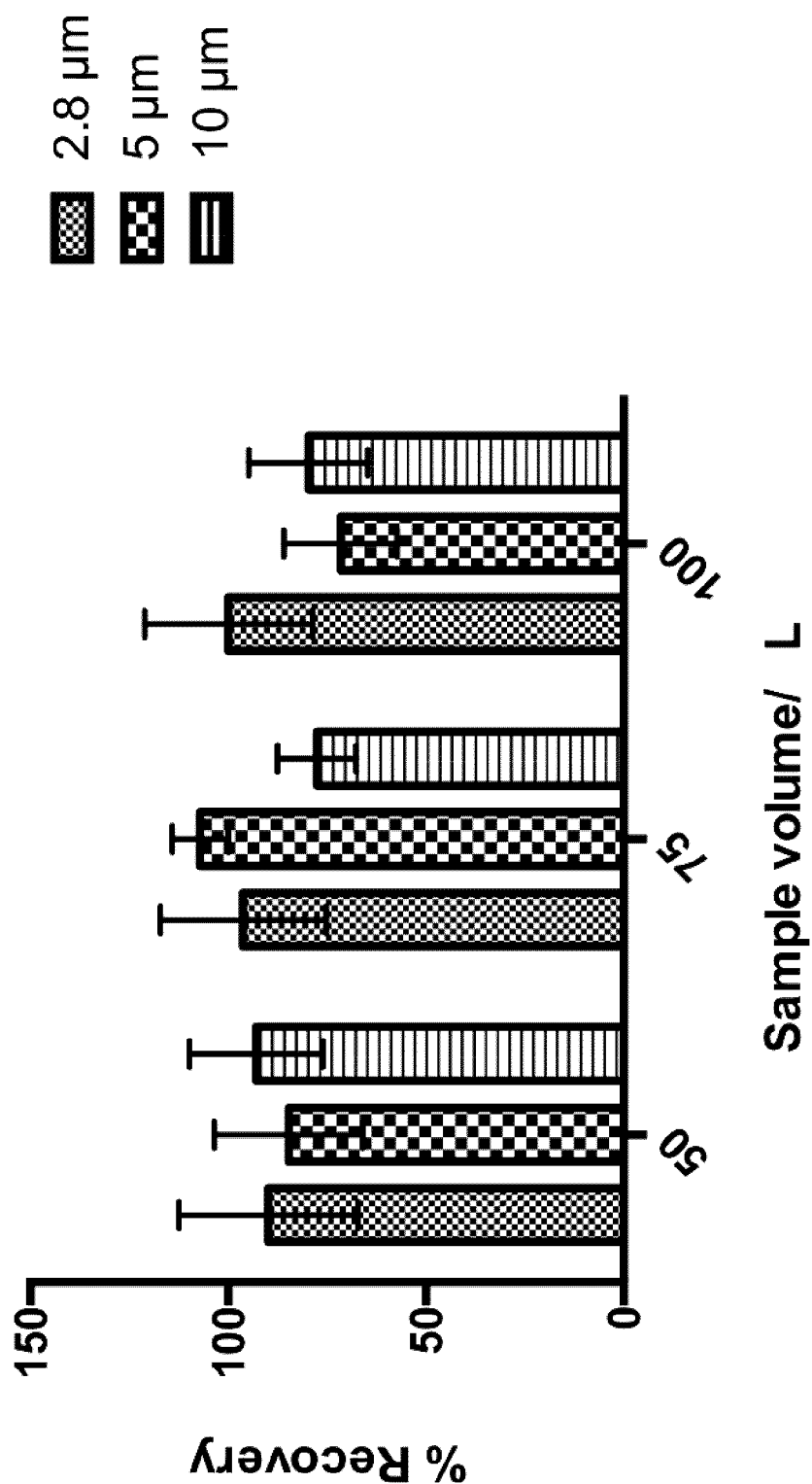
FIG. 4 shows the results of tests exploring the recovery rate of 2.8, 5, and 10 μm magnetic particles from 50, 75, and 100 μL volumes of phosphate buffered saline which presents the mean percentage recovery and the standard deviations across three tests for each condition.

The method of pre-concentrating magnetic particles on DMF was applied to different sample liquids, including phosphate buffered saline, saliva, and urine. In all cases, the method was capable of removing the supernatant liquid and concentrating the particles. The results of further tests exploring the recovery rate of 2.8, 5, and 10 µm magnetic particles from 50, 75, and 100 µL volumes of phosphate buffered saline are shown in FIG. 4. In this test, 2 µL volumes of magnetic particles at densities of $9.00 \times 10^7$ to $1.84 \times 10^8$ were added to a volume of phosphate buffered saline. Particles were then concentrated using the pre-concentration method described here, and recovered particles were counted. FIG. 4 presents the mean percentage recovery and the standard deviations across three tests for each condition.

Figure 5:
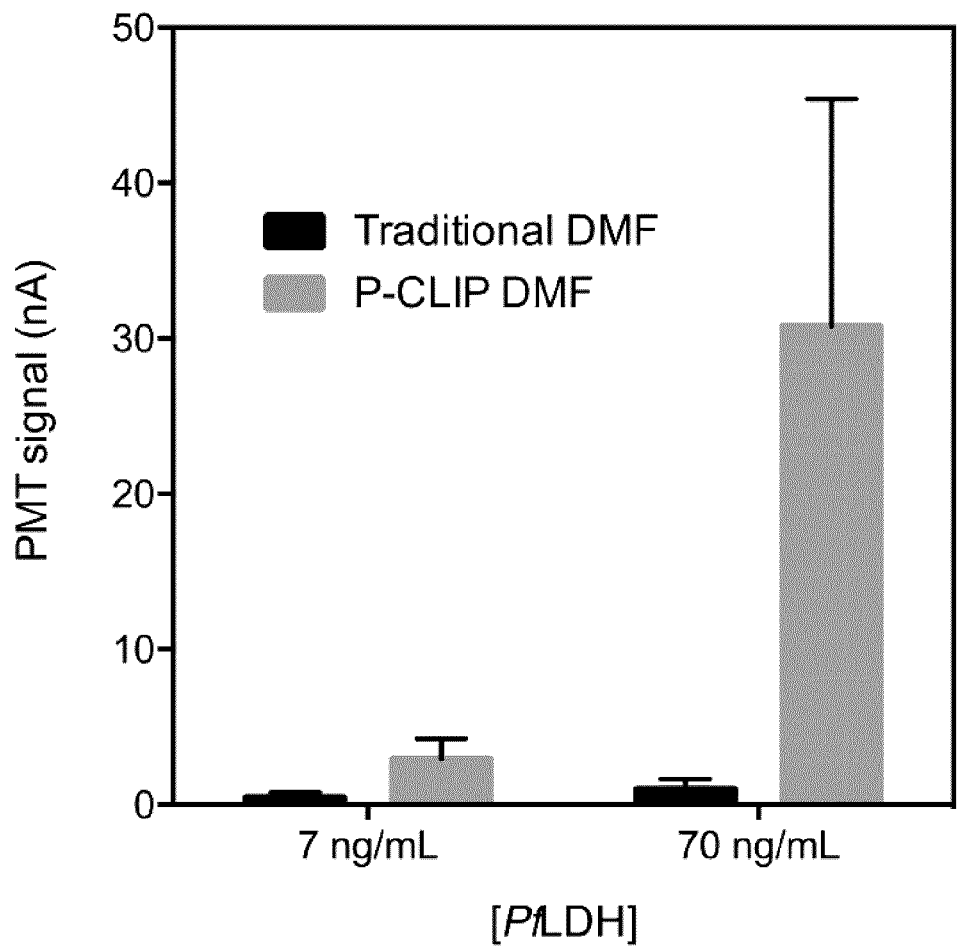
FIG. 5 is a graph showing calibration curves for the standard DMF-ELISA method and the pre-concentration DMF-ELISA process disclosed herein.

The pre-concentration of particles can be used to improve the sensitivities of capture assays such as immunoassays or nucleic acid hybridization assays. A DMF enzyme-linked immunosorbent assay (ELISA) for *Plasmodium falciparum* lactate dehydrogenase (LDH) was performed on-chip using conventional DMF-ELISA protocols and a protocol modified by the addition of the pre-concentration method. A conventional DMF-ELISA was run as a comparison where a 2.4 µL volume of magnetic particles ($6.7 \times 10^8$ particles/ mL) functionalized with anti-PfLDH antibodies was dispensed on the DMF device. The particles were immobilized and the supernatant was removed. The particles were then incubated with 2.4 µL of phosphate buffered saline and the antigen PfLDH. The mixture was incubated for 5 minutes with mixing by the DMF electrodes. The particles were then subjected to the standard DMF-ELISA protocol of washing, incubating with enzyme-conjugated antibody labels, further washing, incubating with chemiluminescent enzyme substrates (luminol and $H_2O_2$), and measuring chemiluminescence with a photomultiplier tube. For the pre-concentration method, a 2.4 µL volume of magnetic particles functionalized with anti-PfLDH antibodies was added to a microcentrifuge tube containing 75 µL phosphate buffered saline and the antigen PfLDH. The mixture was incubated for 3 hours with rotation at room temperature before being processed on a DMF device using the pre-concentration method described here. A longer incubation time was necessary for the pre-concentration method due to the 30-fold decrease in particle concentration. The particles were then subjected to the standard DMF-ELISA protocol. Results comparing the signals from pre-concentration to the conventional DMF-ELISA for concentrations of 7 ng/mL and 70 ng/mL PfLDH are presented in FIG. 5. Signal increases of up to 30-fold were observed.

Discussion

Approaches to magnetic particle-based capture bioassays by DMF involve mixing magnetic microparticles coated with capture agents and a sample on the DMF device. This conventional approach involves dispensing a volume of magnetic particles, removing the supernatant liquid, dispensing a similar-sized volume of sample and mixing the droplet of sample with the magnetic microparticles. The amount of target analyte that can be captured is limited to what is present in the volume of the sample and these volumes are typically on the order of 50 nL to 5 µL. This may be sufficient for detecting a certain range of concentrations of the target analyte within the sample, but will not be sufficient for detecting concentrations of analyte which are below the limit of detection of the analytical detector.

To overcome the challenge of insufficient analyte within the sample, larger volumes can be used, thereby capturing more analyte. This proves difficult to process using the conventional DMF method described above as the maximum volume that can be processed at a time is limited by the size of the DMF device. This could be circumvented by repeatedly mixing the magnetic particles with a droplet of sample, removing the sample from the particles by means of a magnet and repeating the incubation with another droplet. This repetitive process is time consuming, inefficient and requires multiple steps.

Another approach to processing large volumes of sample on a DMF device would be to create a virtual channel defined by a series of driving electrodes and powered by a pump and to use this channel to flow a larger volume of sample over magnetic particles that have been immobilized by a magnetic field on the device. While this method allows larger volumes of sample to be processed, the immobilized particles are clustered within the magnetic field and a limited surface of the particles is exposed to the sample thereby reducing the amount of analyte that is bound. This is inefficient as many of the available binding sites on the magnetic particle are buried within the clump and not exposed to the sample.

The present method disclosed herein overcomes the problem of processing large volumes of sample with magnetic microparticles for bioassays by performing the incubation of the magnetic microparticles with the sample off-chip and then using a combination of a virtual channel on the DMF device and a magnet to concentrate the analytes captured from the larger liquid sample. The volume of sample that can be processed by this method is on the order of 50 to 1000 times greater than the volumes typically processed by DMF and concentrates the analytes into a smaller volume that is amenable to further processing by a DMF device.

Further, when the pump mechanism that drives the virtual channel on the device is a passive pump, such as an absorbent wicking material like filter paper or tissue paper, the need for complicated active pumps and tubing is eliminated. This simplification even allows for the passive pump to be preloaded on the DMF device.

While the present method as exemplified above has been described with respect to increasing the concentration of an analyte of interest which may be present in low concentrations difficult to detect, it will be appreciated that the present method may also be used to screen out or remove analytes which may be considered interferents which when present in high concentrations mask the presence of analytes which need to be detected. In this embodiment the volume of liquid sample that is removed from the magnetic microparticles coated with analyte specific receptors and bound analyte is retained in a container and can be reintroduced to the DMF device for further processing and analysis or delivered to another system for analysis.

REFERENCES

1. K. Aguilar-Arteaga, J. A. Rodriguez and E. Barrado, Analytica Chimica Acta, 2010, 674, 157-165.
2. K. Choi, A. H. C. Ng, R. Fobel and A. R. Wheeler, in Annual Review of Analytical Chemistry, Vol. 5, eds. R. G. Cooks and E. S. Yeung, Annual Reviews, Palo Alto, 2012, vol. 5, pp. 413-440.
3. K. Choi, A. H. C. Ng, R. Fobel, D. A. Chang-Yen, L. E. Yarnell, E. L. Pearson, C. M. Oleksak, A. T. Fischer, R. P. Luoma, J. M. Robinson, J. Audet and A. R. Wheeler, Analytical Chemistry, 2013, 85, 9638-9646.
4. N. M. Lafreniere, J. M. Mudrik, A. H. C. Ng, B. Seale, N. Spooner and A. R. Wheeler, Analytical Chemistry, 2015, 87, 3902-3910.
5. N. S. Mei, B. Seale, A. H. C. Ng, A. R. Wheeler and R. Oleschuk, Analytical Chemistry, 2014, 86, 8466-8472.
6. A. H. C. Ng, K. Choi, R. P. Luoma, J. M. Robinson and A. R. Wheeler, Analytical Chemistry, 2012, 84, 8805-8812.
7. A. H. C. Ng, M. Lee, K. Choi, A. T. Fischer, J. M. Robinson and A. R. Wheeler, Clinical Chemistry, 2015, 61, 420-429.
8. M. H. Shamsi, K. Choi, A. H. C. Ng and A. R. Wheeler, Lab on a Chip, 2014, 14, 547-554.

Therefore what is claimed is:

1. A method for sequestering and concentrating analytes from a volume of liquid sample to a droplet of reagent with a smaller volume, comprising:
   a) exposing magnetic microparticles coated with analyte specific receptors to the volume of liquid sample containing the analytes;
   b) placing the volume of liquid sample containing the magnetic microparticles into a reservoir forming part of a digital microfluidic device;
   c) forming a virtual fluid flow channel across the digital microfluidic device by activating a preselected pattern of driving electrodes with a preselected pattern of voltages across the digital microfluidic device from the reservoir to an exit location from which liquid is to be removed from the digital microfluidic device and at the same time applying a magnetic field at a preselected holding location along the virtual fluid flow channel, wherein upon activating the preselected pattern of driving electrodes, liquid from the volume of liquid sample in the reservoir traverses a distance from the reservoir to the exit location and the magnetic microparticles with the analytes bound to the analyte specific receptors moving from the reservoir, upon reaching the holding location, are substantially held at the holding location by the magnetic field, and remaining liquid remains flowing to the exit location by means of a pumping mechanism to be removed from the digital microfluidic device;

d) dispensing a droplet of a reagent over the magnetic microparticles held at the holding location by the magnetic field, said droplet of reagent having a smaller volume compared to the volume of liquid sample; and e) removing the magnetic field at the holding location either before, during or after step d) such that the magnetic microparticles are released from the holding location and dispersed into the droplet of reagent dispensed over the magnetic microparticles; and wherein the droplet of reagent containing the magnetic microparticles having the analytes bound thereto contains a higher concentration of the magnetic microparticles and analytes as compared to a concentration of the analytes in said volume of liquid sample.

2. The method according to claim 1 wherein the pumping mechanism is a passive pumping mechanism.

3. The method according to claim 2 wherein the passive pumping mechanism is an absorbent wicking medium.

4. The method according to claim 3 wherein the digital microfluidic device is a one plate digital microfluidic device or a two plate digital microfluidic device.

5. The method according to claim 2 wherein the digital microfluidic device is a one plate digital microfluidic device.

6. The method according to claim 2 wherein the digital microfluidic device is a two plate digital microfluidic device.

7. The method according to claim 1 wherein the pumping mechanism is an active pumping mechanism.

8. The method according to claim 7 wherein the digital microfluidic device is a one plate digital microfluidic device.

9. The method according to claim 7 wherein the digital microfluidic device is a two plate digital microfluidic device.

10. The method according to claim 1 wherein the digital microfluidic device is a one plate digital microfluidic device.

11. The method according to claim 1 wherein the digital microfluidic device is a two plate digital microfluidic device.

12. The method according to claim 1 wherein the digital microfluidic device includes a first hydrophilic stripe extending from the reservoir toward a pre-specified location where magnetic microparticles are to be sequestered on the digital microfluidic device, and including a second hydrophilic stripe extending from the exit location toward the same pre-specified location such that there is a gap between the two hydrophilic stripes which is less than a length of an underlying driving electrode on a bottom plate at the pre-specified location where sequestering takes place, and wherein after placing the volume of liquid sample into the reservoir, it is wicked along to the pre-specified location by the first hydrophilic stripe, and by applying a voltage to the driving electrode at the pre-specified location, the liquid sample is bridged to the second hydrophilic stripe and imbibed by the pumping mechanism.

13. The method according to claim 1, wherein, after the step (e), the method comprises a step of further processing the droplet of reagent containing the magnetic microparticles on the digital microfluidic device, wherein the further processing comprises immunoassays, sample cleanup, and/or nucleic acid assays.

14. A system for sequestering and concentrating analytes from a volume of liquid sample to a droplet of reagent with a smaller volume, comprising:

a) a digital microfluidic device having an array of driving electrodes and a pumping mechanism for pumping liquid from a liquid reservoir to an exit location;

b) a magnet positioned to apply a focused magnetic field adjacent to one or more preselected driving electrodes to form a holding location when in operation;

c) computer controller programmed for applying preselected patterns of voltages to said array of driving electrodes;

d) means for exposing magnetic microparticles coated with analyte specific receptors to a volume of liquid sample containing the analytes located remote from said digital microfluidic device and placing the volume of liquid sample containing the magnetic microparticles into the reservoir;

e) the computer controller being programmed for forming a virtual fluid flow channel by activating a preselected pattern of driving electrodes with a preselected pattern of voltages across the digital microfluidic device from the reservoir to the exit location from which liquid is to be removed from the digital microfluidic device while at the same time applying a magnetic field at a preselected holding location along the virtual fluid flow channel, wherein upon activating the preselected pattern of driving electrodes, liquid from the volume of liquid sample in the reservoir traverses a distance from the reservoir to the exit location and the magnetic microparticles with the analytes bound to the analyte specific receptors moving from the reservoir, upon reaching the holding location, are substantially held at the holding location by the magnetic field, and remaining liquid remains flowing to the exit location by means of the pumping mechanism to be removed from the digital microfluidic device;

f) means for dispensing a droplet of a reagent over the magnetic microparticles held at the holding location by the magnetic field, said droplet of reagent having a smaller volume compared to the volume of liquid sample, and means for removing the magnetic field at the holding location such that the magnetic microparticles are released from the holding location and dispersed into the droplet of reagent dispensed over the magnetic microparticles; and g) wherein the droplet of reagent containing the magnetic microparticles having the analytes bound thereto contains a higher concentration of the analytes as compared to a concentration of the analytes in the volume of liquid sample.

15. The system according to claim 14 wherein the pumping mechanism is a passive pumping mechanism.

16. The system according to claim 15 wherein the digital microfluidic device is a one plate digital microfluidic device or a two plate digital microfluidic device.

17. The system according to claim 15 wherein the passive pumping mechanism is an absorbent wicking medium.

18. The system according to claim 14 wherein the pumping mechanism is an active pumping mechanism.

19. The system according to claim 18 wherein the digital microfluidic device is a one plate digital microfluidic device or a two plate digital microfluidic device.

20. The system according to claim 14 wherein the digital microfluidic device is a one plate digital microfluidic device.

21. The system according to claim 14 wherein the digital microfluidic device is a two plate digital microfluidic device.

22. The system according to claim 14 wherein the digital microfluidic device includes a first hydrophilic stripe extending from the reservoir toward a pre-specified location where magnetic microparticles are to be sequestered on the digital microfluidic device, and including a second hydrophilic stripe extending from the exit location toward the same pre-specified location such that there is a gap between the two hydrophilic stripes which is less than a length of an underlying driving electrode on a bottom plate at the pre-specified location where sequestering takes place, and wherein after placing the volume of liquid sample into the reservoir, it is wicked along to the pre-specified location by the first hydrophilic stripe, and by applying a voltage to the driving electrode at the pre-specified location, the liquid sample is bridged to the second hydrophilic stripe and imbibed by the pumping mechanism.

23. The system according to claim 14, further comprising a means for processing the droplet of reagent containing the magnetic microparticles for immunoassays, sample cleanup, and/or nucleic acid assays on the digital microfluidic device.

* * * * *